United States Patent [19]

Brunner et al.

[11] 4,306,082

[45] Dec. 15, 1981

[54] OPTICALLY ACTIVE TERTIARY PHOSPHINE OXIDES AND TERTIARY PHOSPHINES AND PROCESSES FOR THEIR PREPARATION

[75] Inventors: Henri Brunner, Lappersdorf; Willigis Pieronczyk, Regensburg, both of Fed. Rep. of Germany

[73] Assignee: BASF Aktiengesellschaft, Fed. Rep. of Germany

[21] Appl. No.: 124,962

[22] Filed: Feb. 27, 1980

[30] Foreign Application Priority Data

Mar. 3, 1979 [DE] Fed. Rep. of Germany ....... 2908358

[51] Int. Cl.³ .......................... C07F 9/53; C07F 9/50
[52] U.S. Cl. .................................. 568/17; 260/429 R; 564/123
[58] Field of Search ................................... 568/14, 17

[56] References Cited

U.S. PATENT DOCUMENTS 3,769,377 10/1973 Selms .................................... 568/14
3,849,480 11/1974 Knowles et al. .................. 568/17 X
3,949,000 4/1976 Aviron-Violet ...................... 568/17
4,166,824 9/1979 Henderson ............................ 568/17

OTHER PUBLICATIONS

J.A.C.S. 99 5950 (1977).
J.A.C.S. 86 2299 (1964).
Izv. Akad. Nauk, SSSR Ser. Khim (in English) 10 2210 (1974).

Primary Examiner—Helen M. S. Sneed
Attorney, Agent, or Firm—Keil & Witherspoon

[57] ABSTRACT

A process for the preparation of pure optically active tertiary phosphines by resolving the corresponding racemic compounds, wherein the phosphines are first converted to the corresponding phosphine oxides in a conventional manner, the resulting racemic mixtures of the phosphine oxides are reacted in organic solution, in accordance with the principles of enantiomer separation via stereomeric compounds, with an optically pure isomer of a tartaric acid which is mono-acylated or bis-acylated at the alcoholic hydroxyls, the diastereomeric compound which is less soluble in the solvent is separated off, the tartaric acid derivative is split off from the resulting pure diastereomeric compound by means of a base and the resulting optically pure or substantially optically pure phosphine oxides are reduced back to the phosphines in a conventional manner.

The optically active tertiary phosphines may be used as ligands in complex compounds of metals of group VIII of the periodic table, and when such complexes are used as hydrogenating or hydroformylating catalysts they result in substantially stereospecific hydrogenation or hydroformylation of prochiral compounds.

9 Claims, No Drawings

OPTICALLY ACTIVE TERTIARY PHOSPHINE OXIDES AND TERTIARY PHOSPHINES AND PROCESSES FOR THEIR PREPARATION

The present invention relates to optically active tertiary phosphine oxides and tertiary phosphines, processes for their preparation, and the use of the optically active tertiary phosphines, in the form of their complex compounds with metals of group VIII of the periodic table, as catalysts for asymmetric syntheses, such as the asymmetric hydrogenation and hydroformylation of olefinically unsaturated compounds.

It is well known that complex compounds of a metal of group VIII of the periodic table as the central atom (hereafter referred to as Z) and one or more molecules of a tertiary phosphine as ligands are excellent catalysts for the hydrogenation and hydroformylation of olefinically unsaturated compounds.

These reactions, which in principle are applicable to any olefinically unsaturated compounds, can be illustrated by a simple example, which has been chosen with a view to the considerations which follow:

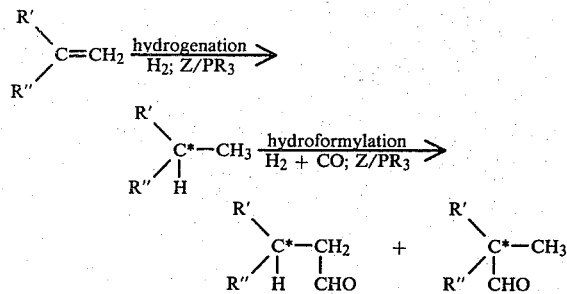

In these equations, R' and R'' are hydrogen or organic radicals and R are the organic radicals of the tertiary phosphine.

As may be seen, the asymmetrical C* atoms can result from these reactions if $R^1$ and $R^2$ differ from one another and from the other two radicals present on this C* atom. If catalysts without phosphine ligands or catalysts containing phosphines such as triphenylphosphine or tributylphosphine as ligands are used, the process yields racemic mixtures as the product.

However, when synthesizing physiologically active compounds, for example drugs, crop protection agents, feedstuffs or fragrance materials, the configuration of these compounds, and hence also the configuration of their intermediates, in most cases matters. It is true that the racemates can be separated by conventional methods via diastereomeric compounds, but such methods are frequently extremely difficult and accordingly expensive, not least because of the fact that equimolar amounts of the optically active resolving agent are needed for resolving the racemate.

It is also known, from the reviews published in Synthesis, 5 (1978), 329 and Pure Appl. Chem., 43 (1975), 401, that the hydrogenation and the hydroformylation of prochiral olefins, ie. of olefins which give products with asymmetric C* atoms, take place substantially stereospecifically if a catalyst of the general type $Z/PR_3$, wherein the tertiary phosphine is a pure optically active compound, is used. If the three radicals R are different, the P atom itself is a chiral center, but the chiral center of the optically active phosphine ligand may also be present at a different point of the molecule.

The use of such catalysts has the advantage of a boosting effect, i.e. small amounts of an optically active catalyst give large amounts of a hydrogenation product or hydroformylation product in which one of the two optical isomers predominates.

However attractive the principle of this process is, its industrial realization presents substantial difficulties, in particular because the tertiary phosphines suitable for the process are difficult to obtain even in the racemate form, and because the resolution of the racemates into their optically active antipodes requires a great deal of experimental work.

It is the principal object of the present invention to provide a generally applicable process for the preparation of optically pure tertiary phosphines. It is a further object of the invention to provide novel phosphines of the above type, which are more easily obtainable than the previously known phosphines, and which, when used as ligands in the complex catalysts employed for the hydrogenation and hydroformylation of prochiral olefins, result in a higher stereospecificity in respect of one of the two optical isomers.

We have found that these objects are achieved and that racemates of optically active tertiary phosphines can be resolved if the phosphines are first converted to the corresponding phosphine oxides in a conventional manner, the resulting racemic mixtures of the phosphine oxides are reacted in organic solution, in accordance with the principles of enantiomer separation via stereomeric compounds, with an optically pure isomer of a tartaric acid which is mono-acylated or bis-acylated at the alcoholic hydroxyls, the diastereomeric compound which is less soluble in the solvent is separated off, the tartaric acid derivative is split off from the resulting pure diastereomeric compound by means of a base and the resulting optically pure or substantially optically pure phosphine oxides are reduced back to the phosphines in a conventional manner.

In an alternative embodiment of the process, the (D,L)-phosphine oxides may be employed directly as starting materials, if they are obtainable by some method other than via the corresponding (D,L)-phosphines.

This generally applicable process is particularly noteworthy because the phosphine oxides, contrary to expectation, give diastereomeric reaction products with the tartaric acid derivatives defined above, these products being most probably hydrogen bridge adducts of the two compounds.

The process may be illustrated by the following diagram:

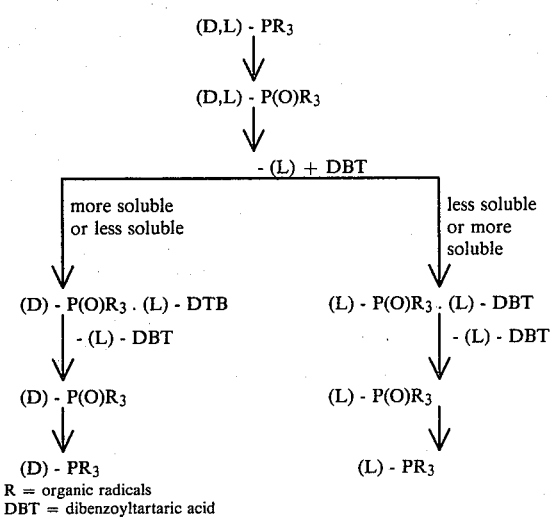

R = organic radicals
DBT = dibenzoyltartaric acid

The process according to the invention can for example be applied to the resolution of the racemates of the following known chiral phosphines:

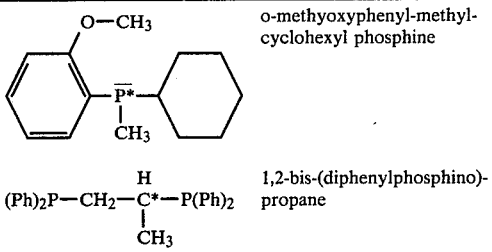

*chirality center
Ph = phenyl

The pure optical isomers of 2,3-bis-(diphenylphosphino)-bicyclo[2,2,1]hept-5-ene (I)

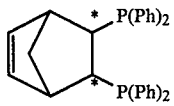

have particularly outstandingly stereospecific catalytic properties. Both the racemate of I and the (D)- and (L)-forms are novel compounds obtainable from conventional intermediates by the process according to the invention. An equimolar amount of the tartaric acid derivative, in particular preferably (−)-(L)-dibenzoyltartaric acid monohydrate ((−)-(L)-DBT) is added to the racemic bis-phosphine oxide (II)

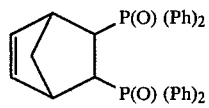

in ethanol solution. The diastereomeric hydrogen bridge adduct (−)-II/(−)-(L)-DBT, hereupon produced as a white precipitate, is less soluble in ethanol, and in most organic solvents, than the diastereomer (+)-II/(−)-(L)-DBT. Examples of suitable solvents other than ethanol are methanol, propanol, isopropanol, butanol, chloroform, methylene chloride, benzene and toluene. The reaction is preferably carried out at room temperature, but can in general be effected at from about 0° to 50° C. If the diastereomer does not precipitate of its own accord, the crystallization can be accelerated by means of a few seed crystals and, where necessary, also by lowering the temperature. The amount of solvent is advantageously such that it just suffices to dissolve II completely. This amount, which is easily determined, corresponds, in the case of the abovementioned solvents, to about 15–30% strength by weight solutions of II.

The crystals and the solution are then worked up in the same manner to give the optical isomers (+)-II and (−)-II, though in the case of the solution the solvent is stripped off, ie. the initially dissolved diastereomer is also converted to the solid form. In both cases, the solid diastereomer is advantageously dissolved or suspended in a solvent which is immiscible with water, for example in chloroform, methylene chloride, benzene or toluene, and a dilute aqueous alkali metal hydroxide solution, for example a solution of KOH or NaOH, is then added to the solution or suspension. This causes the DBT to be split off in the form of its alkali metal salt, which passes into the aqueous phase. The DBT can then be recovered in a conventional manner, for example by passing the solution over an acid ion exchanger. This gives an aqueous solution of DBT, from which the DBT can be recovered in the pure form by stripping off the water or by extraction with ether.

On resolving the diastereomer, the phosphine oxide II passes into the organic phase, from which it can be isolated in a conventional manner. The optical purity after this separation step is about 76%, and can be increased to virtually 100% merely by repeating the process once, ie. the optical rotation no longer increases if further purification steps are carried out.

If the solvent is inert, the solution of II can be directly subjected to the reduction reaction. A particularly suitable reducing agent is trichlorosilane (HSiCl$_3$), as is known from J.Am. Chem. Soc., 99 (1977), 5,950 and the earlier literature quoted there.

The reduction is advantageously carried out with from 4 to 10 moles of HSiCl$_3$ per mole of II, in organic solution, eg. in benzene, at from 60° to 100° C. under a pressure of from 1 to 10 bar, after which an aqueous alkali metal hydroxide solution, for example a solution of NaOH, is added to the mixture at from 5° to 30° C. After separating off the aqueous phase, the solvent is distilled from the organic phase, leaving the phosphine I. The latter can be purified further by recrystallization from acetone.

The known racemic phosphine oxide II may be obtained as follows: Following the method described in J.Am. Chem. Soc., 86 (1964), 2,299, trans-1,2-dichloroethylene is reacted with potassium diphenylphosphine to give the prochiral trans-1,2-diphenylphosphinoethylene

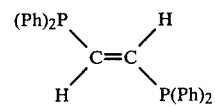

which is oxidized with hydrogen peroxide to give the corresponding phosphine oxide; the latter is converted to the II-racemate by a Diels-Alder reaction with cyclopentadiene, using the method described in Izv. Akad. Nauk SSSR Ser. Khim (in English), 10 (1974), 2,210.

The methods described for the example of the preparation of I and its pure optical isomers apply equally to the use of the other tartaric acid derivatives, which can be, quite generally, any tartaric acid in which the alcoholic hydroxyls are mono-acylated or bis-acylated. The acyl radicals may be derived from aliphatic, aromatic, cycloaliphatic and araliphatic organic acids, preferably of 1 to 12 carbon atoms, which in turn may carry inert substituents. Amongst these resolving agents, dibenzoyltartaric acid has proved particularly suitable.

In a modified version of the separation process, it is frequently also possible to start from a half-molar amount of (L)-DBT per mole of racemic II. In that case, only the less soluble diastereomer (−)-II/(−)-(L)-DBT is obtained, whilst the antipode (+)-II remains in solution.

The methods described are applicable—where necessary after some exploratory experiments—to the preparation of any optically pure phosphines from the racemic phosphines or phosphine oxides.

As is well known, tertiary phosphines and metals Z of group VIII of the periodic table form complex compounds of the type

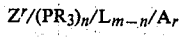

where L may be other ligands, n is from 1 to m and m is the total valency, in respect of ligands, of the central atom Z, r is the valency of the central atom and A is an anion. For hydrogenation, suitable metals Z are in the main ruthenium, iridium, palladium, platinum and cobalt and especially rhodium, whilst for hydroformylation suitable metals Z are rhodium and cobalt. Examples of other ligands are cyclooctadiene, acetylacetone and carbon monoxide. The metals Z can be present in a zero-valency form (r=0) or, as a salt-like complex, in a higher-valency form. In the latter case, additional components present in the complex compounds are the anions A, eg. Cl− or Br−, in a number corresponding to the valency.

Numerous complex compounds of this type, and their preparation, have been disclosed. Where $PR_3$ is an optically active ligand, this naturally does not introduce any special features. The same is true of the method of hydrogenation and of hydroformylation, so that further details thereof are unnecessary. Frequently, complexes of this type, or similar complexes, will form in situ under the reaction conditions, so that it suffices to introduce a salt of Z, or a phosphine-free complex of Z, and the phosphine separately into the reaction batch. As with other hydrogenations and hydroformylations, it may be advantageous to have free phosphine present in an excess of up to about 10 moles over the complex compound.

In accordance with the object of the invention, the stereospecific catalysts are of course only used for the hydrogenation or hydroformylation of prochiral olefinically unsaturated compounds, as illustrated at the outset in relation to the example of the olefin R'R''C=CH$_2$. Of course, this also applies to olefins of the type R'R''C=CR'''R'''', where under certain circumstances two chiral centers may also result. Further, it is to be borne in mind that the hydroformylation as a rule results in isomer mixtures, depending on the carbon atom at which the formyl group enters the molecule. However, in every case predominantly one of the optical isomers results, and optical purities of up to 95% can be achieved, depending on the tendency of the particular products to racemize. For practical purposes, however, even optical purities from about 10% upward may be of commercial importance.

EXAMPLE 1 trans-(−)-2,3-Bis-(diphenylphosphine-oxido)-bicyclo-[2,2,1]-hept-5-ene; (−)-II

A solution of 19.5 g of (−)-(L)-dibenzoyltartaric acid monohydrate ((−)-(L)-DBT) in 20 ml of ethanol was added to a solution of 25.5 g of racemic II and 105 ml of 99% strength ethanol at room temperature. The molar ratio of II to DBT was 1:1.

After about 2 minutes, the less soluble diastereomer (−)-II/(−)-(L)-DBT began to separate out as a white precipitate. The diastereomer formation was complete after 1 hour. The more soluble diastereomer (+)-II/(−)-(L)-DBT remained in solution.

The dry precipitate (yield about 43%) was then taken up in 100 ml of chloroform and stirred vigorously with a solution of 4 g of KOH in 160 ml of water.

The aqueous phase was separated off and washed once with 30 ml of chloroform. The two chloroform phases were combined, dried and freed from chloroform by distillation at room temperature.

The crude yield of (−)-II was 43% (=11 g).

Optical rotation of the crude product: $[\alpha]_{578}^{20}$ (c=1; chloroform) = −47°

Repeating this separation process once gave pure (−)-II in 35% yield and a virtually completely pure form, since no further increase in optical rotation was observed on further repetitions of the process.

(−)-II, optical rotation: $[\alpha]_{578}^{20}$ (c=1, chloroform) = −62°

EXAMPLE 2 trans-(+)-2,3-Bis-(diphenylphosphine-oxido)-bicyclo-[2,2,1]-hept-5-ene; (+)-II

The solution of the more soluble diastereomer (+)-II/(−)-(L)-DBT in ethanol, obtained as described in Example 1, was concentrated, and the residue was then stirred with 100 ml of anhydrous acetone. This did not cause the residual less soluble diastereomer to dissolve. This residue was separated off (4.5 g), after which the diastereomer which had remained in solution was worked up as described in Example 1 to give (+)-II.

Optical rotation of pure (+)-II: $[\alpha]_{578}^{20}$ (c=1; chloroform) = +58°

EXAMPLE 3 trans-(+)-2,3-Bis-(diphenylphosphino)-bicyclo-[2,2,1]-hept-5-ene; (+)-I

A mixture of 9 g of racemic II, 15 g of trichlorosilicon hydride and 200 ml of benzene was heated for 15 hours at 75° C. under autogenous pressure (about 3 bar). After distilling off the excess Si compound, the residue was taken up in 100 ml of benzene and sufficient 25% strength by weight sodium hydroxide solution was added dropwise, at 6° C., to redissolve the initially formed precipitate (probably consisting of SiOH compounds). The benzene phase was washed with water and dried, after which the benzene was distilled off. The residue was recrystallized from hot acetone. The yield of (+)-I was 75%.

EXAMPLE 4 trans-(−)-2,3-Bis-(diphenylphosphino)-bicyclo[2,2,1]-hept-5-ene; (−)-I

Using the method of Example 3, (−)-II was reduced to optically pure (−)-I; melting point 129°–130° C. Optical rotation $[\alpha]_{578}^{20}$ (c=1; chloroform)= −43.5°

EXAMPLE 5 trans-(+)-2,3-Bis-(diphenylphosphino)-bicyclo-[2,2,1]-hept-5-ene; (+)-I

Using the method of Example 3, (+)-II was reduced to optically pure (+)-I; melting point 129°–130° C. Optical rotation $[\alpha]_{578}^{20}$ (c=1; chloroform)= +45°

EXAMPLE 6

Preparation of (D-)-N-acetylphenylalanine

To prepare a stereospecific hydrogenation catalyst, 7 mg ($1.4 \times 10^{-5}$ mole) of the complex compound bis-(cyclooocta-1,5-diene)-$\mu,\mu'$-dichlorodirhodium

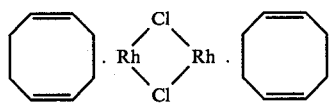

and 14.5 mg ($3.1 \times 10^{-5}$ mole) of (+)-I were dissolved in 5 ml of methanol and the solution was stirred for 30 minutes. This resulted in a yellowish orange solution of a complex compound of the initial Rh complex and the phosphine.

This catalyst solution was mixed with a solution of 500 mg ($2.4 \times 10^{-3}$ mole) of the prochiral compound (Z)-α-[N-acetamino]-cinnamic acid

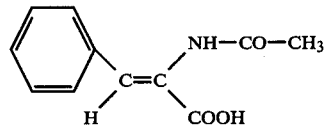

and hydrogenation was then carried out in a conventional manner at room temperature under a hydrogen pressure of from 1 to 1.2 bar. The hydrogen uptake was about 50 ml.

The solution was then evaporated to dryness under reduced pressure, after which the residue was taken up in 5 ml of 0.5 N aqueous sodium hydroxide solution. This decomposed the catalyst, the components of which gave a solid residue. This residue was washed with three times 3 ml of water. The alkaline solution and the wash water were combined, acidified slightly with 2.6 ml of 1 N HCl and then extracted with ether. Conventional working up of the ether extract phase gave N-acetylphenylalanine in virtually quantitative yield, the optical yield in respect of the (D-)-isomer being about 95% calculated from the optical rotation given in the literature (Tetrahedron Letters 52, (1977), 4,639).

EXAMPLE 7

Preparation of (L+)-N-acetylphenylalanine

This compound was prepared, in the same yield and the same purity as (D-)-N-acetylphenylalanine by using the method described in Example 6 but employing the antipode catalyst component (−)-I.

EXAMPLE 8

Preparation of (−)-1,2-bis-diphenylphosphine-oxidopropane; III 12.5 g of (−)-(L)-DBT were added at room temperature to a solution of 15.9 g of racemic III in 75 ml of 99% strength ethanol. The molar ratio of the two diastereomer components was 1:1. After stirring the mixture for 20 hours, 4.2 g of the less soluble diastereomer (−)-III/(−)-(L)-DBT were separated off, dried and dissolved in a mixture of 10 ml of 1 N NaOH and 40 ml of chloroform. 2 g of enriched (−)-III were isolated from the organic phase.

Optical rotation $[\alpha]_{578}^{20}$ (c=1; chloroform): −8°.

EXAMPLE 9

Preparation of (+)-2-phenylpropanal 100 g of styrene in 600 ml of toluene as the solvent were hydroformylated, in a high-pressure autoclave of 1 liter capacity, for 12 hours with a mixture of 45% by volume of CO and 55% by volume of $H_2$ at 80° C. and 200 bar in the presence of 50 g of dimeric rhodiumcarbonyl chloride and 250 mg of (+)-II. Conventional working up of the reaction mixture gave the optically inactive 3-phenylpropanal in about 9% yield and a mixture of the optical isomers of 2-phenylpropanal in about 78% yield. According to the optical rotation $[\alpha]_D^{20}$ (c=1; chloroform)= +48° C., the optical purity of the 2-phenylpropanal was 22%.

We claim:

1. A process for the preparation of pure optically active tertiary phosphines by resolving the corresponding racemic mixtures of phosphine oxides, wherein
   the racemic mixtures of the phosphine oxides are reacted in organic solution, in accordance with the principles of enantiomer separation via stereomeric compounds, with an optically pure isomer of a tartaric acid which is mono-acylated or bis-acylated at the alcoholic hydroxyls,
   the diastereomeric compound which is less soluble in the solvent is separated off,
   the tartaric acid derivative is split off from the resulting pure diastereomeric compound by means of a base and
   the resulting optically pure or substantially optically pure phosphine oxides are reduced to the tertiary phosphines.

2. A process as claimed in claim 1, wherein trans(D,L)-2,3-bis-(diphenylphosphine-oxido)-bicyclo[2,2,1]-hept-5-ene is resolved.

3. A process as claimed in claim 1 or 2, wherein (D)- or (L)-dibenzoyltartaric acid is used as the resolving agent.

4. trans-(D)-2,3-Bis-(diphenylphosphine-oxido)-bicyclo[2,2,1]-hept-5-ene.

5. trans-(L)-2,3-Bis-(diphenylphosphine-oxido)-bicyclo-[2,2,1]-hept-5-ene.

6. Racemic trans-2,3-bis-(diphenylphosphino)-bicyclo-[2,2,1]-hept-5-ene.

7. trans-(D)-2,3-Bis-(diphenylphosphino)-bicyclo-[2,2,1]-hept-5-ene.

8. trans-(L)-2,3-bis-(diphenylphosphino)-bicyclo-[2,2,1]-hept-5-ene.

9. The process of claim 1, wherein trichlorosilane is used as the agent for reducing the phosphine oxides to the optically active tertiary phosphines.